US010167412B2

(12) United States Patent
Allais et al.

(10) Patent No.: US 10,167,412 B2
(45) Date of Patent: Jan. 1, 2019

(54) PHENOL POLYMER WITH 5,5'-BIARYL BONDS, METHOD FOR PREPARING SAME, AND USES THEREOF

(71) Applicants: INSTITUT NATIONAL DE LA RECHERCHE AGRONOMIQUE, Paris (FR); INST SCIENCES IND VIVANT ENVIRONNEMENT, Paris (FR)

(72) Inventors: Florent Allais, Bouy (FR); Florian Pion, Plerin (FR); Armando Reano, Reims (FR); Paul-Henri Ducrot, Igny (FR); Henry Eric Spinnler, Sevres (FR)

(73) Assignees: INSTITUT NATIONAL DE LA RECHERCHE AGRONOMIQUE, Paris (FR); INST SCIENCES IND VIVANT ENVIRONNMENT, Paris (FR)

( * ) Notice: Subject to any disclaimer, the term of this patent is extended or adjusted under 35 U.S.C. 154(b) by 0 days.

(21) Appl. No.: 15/028,812

(22) PCT Filed: Oct. 13, 2014

(86) PCT No.: PCT/FR2014/052604
§ 371 (c)(1),
(2) Date: Apr. 12, 2016

(87) PCT Pub. No.: WO2015/055936
PCT Pub. Date: Apr. 23, 2015

(65) Prior Publication Data
US 2016/0257846 A1    Sep. 8, 2016

(30) Foreign Application Priority Data

Oct. 14, 2013 (FR) ...................... 13 59948

(51) Int. Cl.
*C09D 167/04* (2006.01)
*C12P 17/18* (2006.01)
*C12P 7/22* (2006.01)
*C12P 7/62* (2006.01)

(52) U.S. Cl.
CPC ............. *C09D 167/04* (2013.01); *C12P 7/22* (2013.01); *C12P 7/62* (2013.01); *C12P 17/181* (2013.01)

(58) Field of Classification Search
None
See application file for complete search history.

(56) References Cited

U.S. PATENT DOCUMENTS 3,388,098 A * 6/1968 Harding .................. C08G 59/26
523/122

FOREIGN PATENT DOCUMENTS

| EP | 1 169 922 A1 | 1/2002 |
| EP | 1 731 043 A1 | 12/2006 |
| WO | 96/03440 A1 | 2/1996 |
| WO | 97/27221 A1 | 7/1997 |
| WO | 03/037829 A2 | 5/2003 |
| WO | 2004/083256 A1 | 9/2004 |

OTHER PUBLICATIONS

NPL Patel J. Indian Chem Soc V. 90 pp. 2169-2179.*
Pion et al. Polymer Preprints 2012, 53(2), 264.*
Pion, Polymer Preprints, 2012 65(4), p. 264.*
Pion et al. RSC Adv., 2013, 3, 8988-8997.*
Kunamneni et al., "Engineering and Applications of fungal laccases for organic synthesis", 2008, Microbial Cell factories 7:32.
Pion et al., "Chemo-enzymatic preparation of new bio-based bisand trisphenols: new versatile building blocks for polymer chemistry", 2013, RSC Advances 3, pp. 8988-8997.
Brand-Williams et al., "Use of a Free Radical Method to Evaluate Antioxidant Activity", 1995, Food Sci. Technol—Leb 28, pp. 25-30.
Molina-Molina et al., "Profiling of benzophenone derivatives using fish and human estrogen receptor-specific in vitro bioassays", 2008, Toxicol. Appl. Pharmacol. 232, pp. 384-395, doi: 10.1016/j.taap.2008.07.017.
Escande et al., "Evaluation of ligand selectivity using reporter cell lines stably expressing estrogen receptor alpha or beta", 2006, Biochemical Pharmacology 71, pp. 1459-1469.
International Search Report, dated Dec. 22, 2014, from corresponding PCT Application.

* cited by examiner

*Primary Examiner* — Robert T Butcher
(74) *Attorney, Agent, or Firm* — Young & Thompson

(57) ABSTRACT

A phenol polymer is obtainable by oligomerization of one or more macropolyphenols serving as monomers, wherein the oligomerization step is catalyzed by an oxidase enzyme. The bonds between the macropolyphenol fragments in the polymer are exclusively 5,5-biaryl bonds. This polymer is useful as an antioxidant, chelating agent, plasticizing agent, or antimicrobial agent.

17 Claims, 7 Drawing Sheets

PHENOL POLYMER WITH 5,5'-BIARYL BONDS, METHOD FOR PREPARING SAME, AND USES THEREOF

The present invention falls within the field of phenol polymers. More particularly, it relates to a phenol polymer, the base monomers of which are macropolyphenols, in particular macrobisphenols, and in which the bonds between monomers are exclusively of 5,5-biaryl type. The invention also relates to a process for synthesizing such a polymer and to a composition containing same, and also to the use of such a phenol polymer, in particular as an antioxidant, free-radical scavenger, antimicrobial agent, chelating agent or plasticizer.

The use of white biotechnologies, i.e. biotechnologies using a biological system, in particular an enzymatic system, for the synthesis of molecules, is of increasing interest, compared with conventional chemical processes, owing to the economical and environmentally friendly nature of these systems. This interest is all the greater when it is possible to use biobased synthons, for example derived from plant biomass, as raw materials for synthesizing molecules.

Many studies have thus, over the past few years, related to the use of enzymes for the catalysis of reactions that were conventionally carried out by chemical processes. Among these studies, some have taken an interest in enzymes of the oxidase type, and more particularly in laccases, for performing oxidative couplings of compounds with a phenol, polyphenol or aniline group. This is in particular the case with the study described in the publication by Kunamneni et al., 2008 (Microbial Cell Factories, 7:32).

However, attested in particular by this publication, in which it is shown that the oxidation of estradiol by a laccase leads to the formation of four different dimer compounds, the oxidative phenolic coupling catalyzed by enzymes of oxidase type has a regioselectivity that is extremely difficult to control, since the coupling of the phenol units to one another can take place on several respective sites of the base molecules.

As it happens, it would be advantageous to have phenol polymer compounds obtained by coupling of phenol molecules, in particular of macropolyphenols, and in particular of macrobisphenols, this coupling preferably being carried out enzymatically, and in any event in a simple and controlled manner so as to ensure the formation of a single polymer product and the presence, in this polymer, of numerous free phenol functions. Indeed, this presence, associated in particular with the aromatic nature of the polymer and with its high molecular weight, would make the latter an ideal candidate as an antioxidant, free-radical scavenger, antimicrobial agent, chelating agent and/or plasticizer. This is the objective targeted by the present invention.

Entirely advantageously and surprisingly, it has now been discovered by the present inventors that this objective can be achieved, and that polymer compounds having numerous free phenol functions, and having considerable antioxidant, free-radical scavenging, antimicrobial, chelating and/or plasticizing properties, can be obtained in a simple and controlled manner by oligomerization catalyzed by an enzyme of oxidase type, from macropolyphenols corresponding to a particular structure.

Thus, the present inventors propose a phenol polymer which can be obtained by oligomerization catalyzed by an enzyme of oxidase type, in particular a laccase, of one or more macropolyphenol(s) each corresponding to general formula (I):

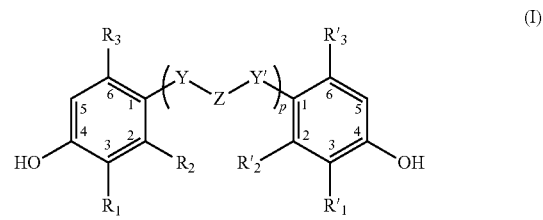

wherein:
p represents an integer between 1 and 30,
$R_1$, $R'_1$, $R_2$, $R'_2$, $R_3$ and $R'_3$, which may be identical or different, each represent a hydrogen atom, a chlorine atom, a bromine atom, an iodine atom, a fluorine atom, or an alkyl, benzyl, Xalkyl, where appropriate substituted, Xbenzyl, where appropriate substituted, Xacyl, B(OR')$_2$, NHR', NO$_2$, SR'O or SO$_2$R' group,
where X represents N, O, S or P
and R' represents an alkyl group or an aryl group,
$R_1$ and $R'_1$ do not represent a hydrogen atom,
Y and Y', which may be identical or different, each represent:
either an oxygen atom, a sulfur atom or a deconjugating group comprising neither an epoxide ring, nor an aziridine ring, nor a phenol group which is not substituted on all its carbon atoms, or a group corresponding to formula (II):

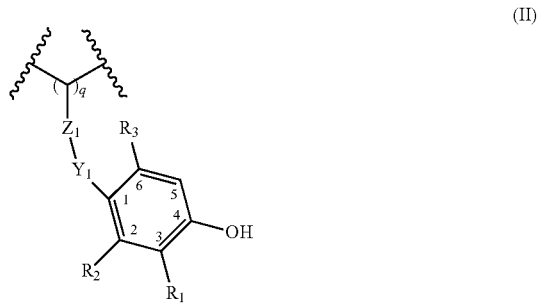

wherein:
q represents an integer between 1 and 8,
$Y_1$ represents an oxygen atom, a sulfur atom or a deconjugating group comprising neither an epoxide ring, nor an aziridine ring, nor a phenol group which is not substituted on all its carbon atoms,
$Z_1$ represents a heteroatom or a spacer group comprising neither an epoxide ring, nor an aziridine ring, nor a phenol group which is not substituted on all its carbon atoms, nor an alkenyl group, nor an alkynyl group,
and $R_1$, $R_2$ and $R_3$ are as defined above,
and Z represents:
either a heteroatom or a spacer group comprising neither an epoxide ring, nor an aziridine ring, nor a phenol group which is not substituted on all its carbon atoms, nor an alkenyl group, nor an alkynyl group, or a group corresponding to formula (III):

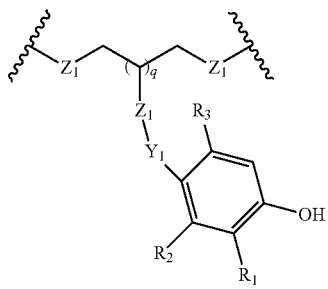

wherein q is an integer between 1 and 8, and $R_1$, $R_2$, $R_3$, $Y_1$ and $Z_1$ are as defined above, the bonds between the macropolyphenol fragments of general formula (I) within said polymer being exclusively 5,5-biaryl bonds.

In the rest of the present description, the term "macrobisphenol" will be used to denote the macropolyphenol of formula (I) when Y and Y' do not represent a group corresponding to formula (II) above and Z does not represent a group corresponding to formula (III) above.

In the present description, the term "deconjugating group" is intended to mean a group not comprising a bond conjugated with the phenol ring, and thus producing a rupture of conjugation between the phenol ring and the group Z, by rupture of the overlap of the pi orbitals between the latter.

The term "polymer" is herein intended to encompass both the polymers stricto sensu, i.e. formed from one and the same monomer, and the copolymers, in particular random copolymers, formed from a plurality of monomers, each however corresponding to general formula (I), for example from 2 or 3 different monomers, or more.

The polymer according to the invention may be of both linear type and branched type, and in particular crosslinked type.

The expression "comprising neither ( . . . ) nor a phenol group which is not substituted on all its carbon atoms" is intended to mean that Z, $Z_1$, Y, Y' and $Y_1$ may comprise a phenol group, but only if all the carbon atoms of the aromatic ring are substituted therein, i.e. are bonded to an atom other than a hydrogen atom.

Entirely advantageously and surprisingly, although it might have been thought, as suggested in particular by the publication by Kunamneni et al., 2008, that the polymerization between the macropolyphenols of general formula (I) would take place between several different sites of the molecules, and would give rise to various types of coupling, in particular, in addition to the 5,5-biaryl couplings, 1,1-, 5,1- or else 4-O-5-biaryl couplings, the polymer compound according to the invention comprises only one type of bond between the macropolyphenol fragments of general formula (I) which form the constituent monomers thereof, more specifically a 5,5-biaryl bond. This bond advantageously does not affect the phenol functions of the macropolyphenols, which remain free and therefore reactive.

In addition, although it might also have been thought that the enzymatic coupling reaction would take place between two phenol rings of the same macropolyphenol fragment of general formula (I), such an intramolecular reaction being kinetically favored by very close spatial proximity of the radicals, it has been noted by the present inventors that, on the contrary, and unexpectedly, an intermolecular coupling occurs substantially exclusively in the reaction medium, resulting in the formation of a polymer.

In the embodiments wherein the starting monomer(s) is (are) macrobisphenols, the polymer according to the invention also has, entirely advantageously, a linear or cyclic homogeneous structure with a controlled degree of polymerization and numerous free phenol functions distributed uniformly along the polymer chain. As a result, this polymer has in particular strong antioxidant, plasticizing, free-radical scavenging and antimicrobial properties. In cyclic form, this polymer also has chelating properties.

When Z represents a group corresponding to formula (III) above, or Y or Y' represents a group corresponding to formula (III) above, i.e. at least one macropolyphenol of general formula (I) is not a macrobisphenol, the polymer according to the invention has a branched structure. Such a polymer also advantageously has a large number of free phenol functions, and, in particular, good plasticizing properties, in particular owing to its aromatic nature and its high molecular weight.

The polymer according to the invention constitutes in particular an advantageous substitute for bisphenol A and derivatives thereof.

Preferentially, each macropolyphenol of general formula (I) is a biobased compound, in particular derived from plant biomass, and in particular from lignocellulosic biomass. The polymer according to the invention, formed from such a base monomer, then advantageously exhibits a renewable nature and a potentially low or zero toxicity, which makes it entirely suitable for use in fields such as that of the food sector or the cosmetics industry.

Examples of such biobased macropolyphenols are in particular described in the publication by Pion et al., 2013 (RSC Advances, 3, 8988-8997).

In general formula (I) above, $R_1$ and/or $R'_1$ preferably represent(s) a linear or branched, saturated hydrocarbon-based radical comprising from 1 to 5 carbon atoms, for example a tert-butyl radical, or an $OR_4$ group, where $R_4$ represents a linear or branched, saturated hydrocarbon-based radical comprising from 1 to 5 carbon atoms, for example a methyl radical.

Preferentially, $R_2$, $R_3$, $R'_2$ and/or $R'_3$ represent(s) a hydrogen atom.

In general formula (I) above, Y and Y' may represent any deconjugating group devoid of an epoxide ring, of an aziridine ring and of a phenol ring which is not substituted on all its carbon atoms. It falls within the competence of those skilled in the art to identify the groups corresponding to such a definition. For example, Y and/or Y' may represent a group of general formula (V):

$$(CH_2)_m—X'— \qquad (V)$$

wherein m is between 1 and 5 and X' represents an oxygen atom or a sulfur atom or a group chosen from the groups:

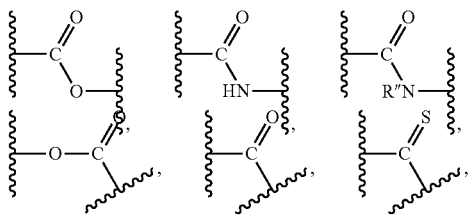

NR", NH or $SO_2$, where R" represents an alkyl group or an aryl group.

$Y_1$ also preferably corresponds to such a definition.

In variants of the invention, in general formula (I), Y and Y', and where appropriate $Y_1$, each represent a group of general formula (VI):

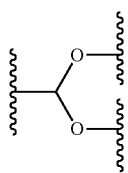
(VI)

The phenol polymer according to the invention is then advantageously biodegradable, in particular in an aqueous medium.

Z, for its part, preferably represents a linear or branched, saturated hydrocarbon-based group, where appropriate substituted, comprising from 1 to 6 carbon atoms, which can comprise one or more heteroatoms, or a saturated cyclic hydrocarbon-based group, where appropriate substituted, comprising from 1 to 6 carbon atoms, which can comprise a single ring or several condensed rings, and which can comprise one or more heteroatoms.

$Z_1$ also preferably corresponds to such a definition.

In particular embodiments of the invention, Z, and where appropriate $Z_1$, are chosen from the following groups (VIIIa) to (VIIIf):

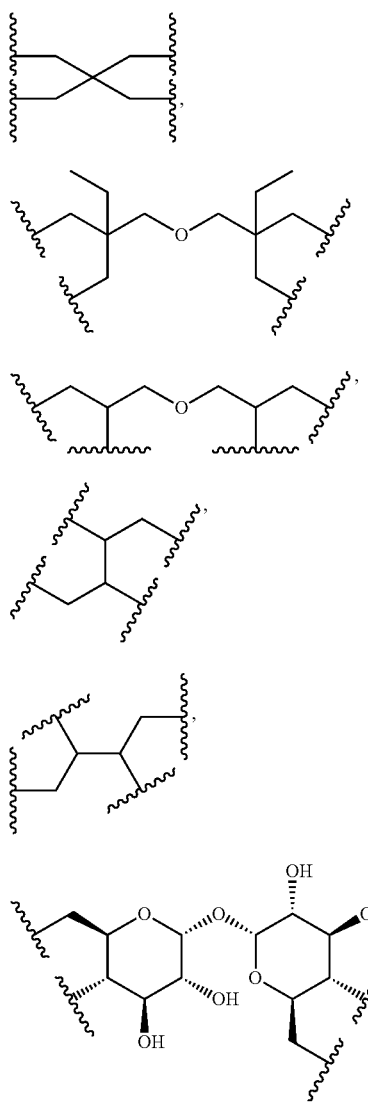

Such a definition of Z, and where appropriate of $Z_1$, proves in particular to be entirely advantageous in combination with the characteristic according to which Y and Y', and where appropriate $Y_1$, each represent a group of general formula (VI) above.

The polymer according to the invention may in particular correspond to general formula (IV):

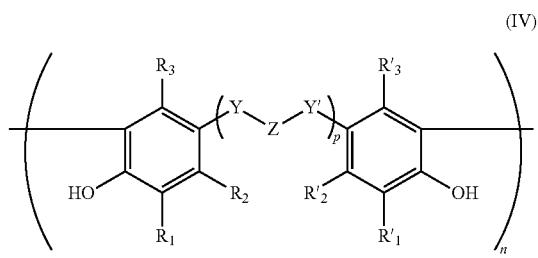

wherein n represents an integer between 2 and 100.

This compound can be both linear or cyclic.

By way of example, starting from the biobased macro-bisphenols described in the publication by Pion et al., 2013, polymers in accordance with the invention, of respective general formulae (IVa), (IVb), (IVc) and (IVd) below, are in particular obtained:

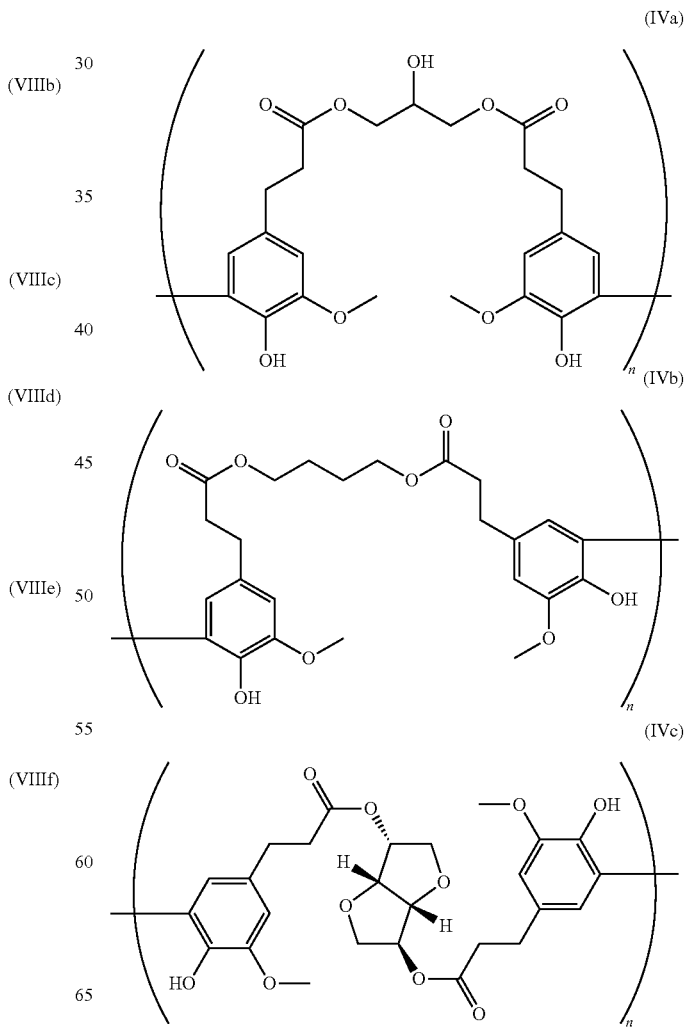

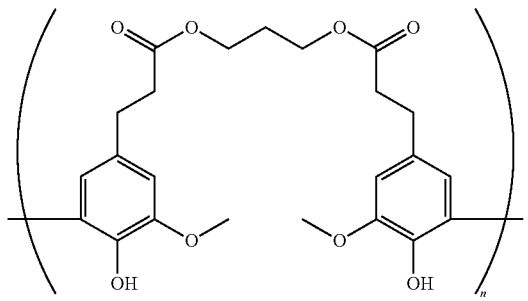

wherein n represents an integer between 2 and 100.

These polymers advantageously all have a low toxicity for living organisms.

The polymer according to the invention may in particular correspond to general formula (VII) below:

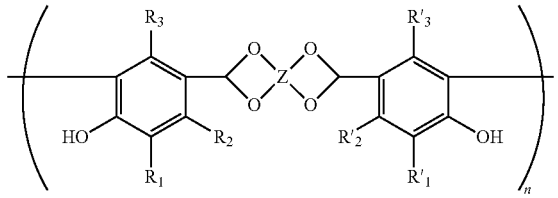

wherein n represents an integer between 2 and 100, and $R_1$, $R_2$, $R_3$, $R'_1$, $R'_2$, $R'_3$ and Z are as defined above.

Examples of such polymers correspond to general formulae (VIIa) to (VIIf) below:

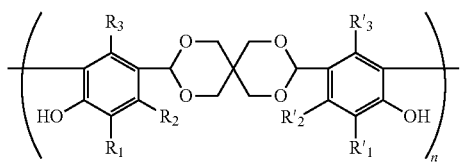

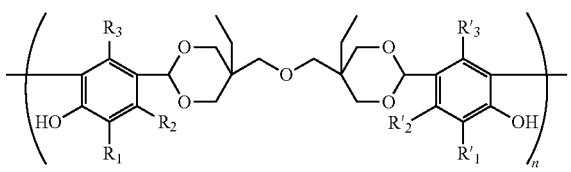

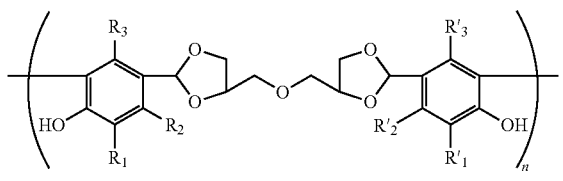

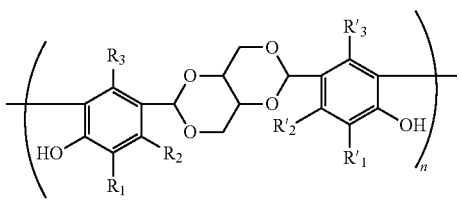

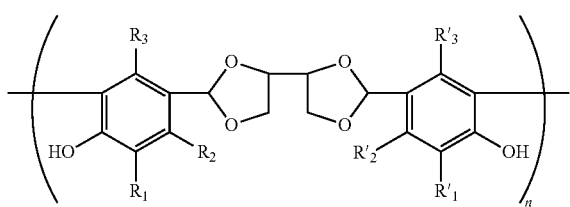

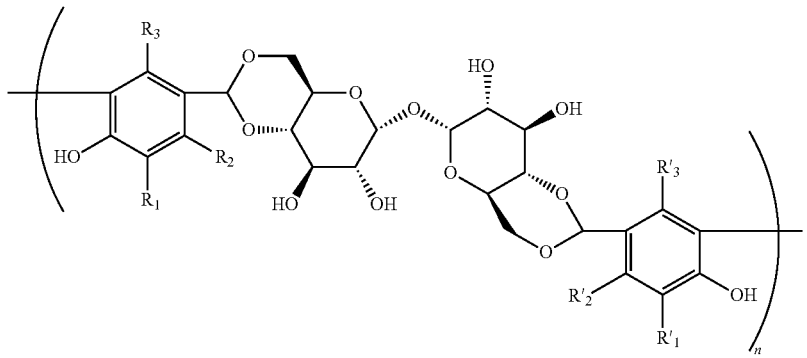

Another example of a polymer in accordance with the present invention corresponds to formula (VIIg) below:

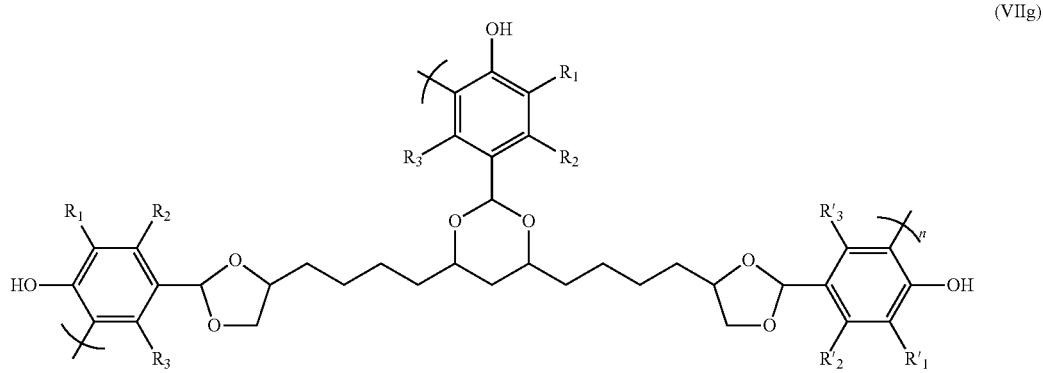

(VIIg)

In addition to oligomerization catalyzed by an enzyme of oxidase type, the phenol polymers according to the invention, for example the polymers corresponding to general formulae (VII), (VIIa), (VIIb), (VIIc), (VIId), (VIIe), (VIIf) and (VIIg) above, can be obtained by any other synthesis route, the step or steps of which is or are conventional in itself or themselves for those skilled in the art.

According to another aspect, the present invention relates to a process for synthesizing a phenol polymer according to the invention, which comprises a step of oligomerization of one or more macropolyphenol(s) each corresponding to general formula (I) above, catalyzed by an enzyme of oxidase type.

Such a process, which falls within the field of white biotechnologies, is advantageously simple and inexpensive to carry out, in particular compared with the conventional chemical processes that would require, in order to achieve the same result, numerous reactions for protection/deprotection of the reactive phenol functions of the macropolyphenol(s). It also makes it possible in particular to control the degree of polymerization of the base macropolyphenol(s), in particular by appropriate control of the reaction time and of the nature and the amount of the cosolvent. When the macropolyphenol(s) is (are) of biobased origin, the process according to the invention additionally proves to be entirely advantageous from an ecological point of view.

Any enzyme of the oxidase family can be used to catalyze the reaction. A peroxidase, such as horseradish peroxidase, can in particular be used.

In preferred embodiments of the invention, the enzyme is a laccase. The laccases are enzymes well known in themselves, belonging to the oxidase class, and present in plants and fungi. They catalyze oxidations of an electron of electron-rich substrates, such as phenol substrates, using atmospheric oxygen as oxidizing agent. The resulting radicals can then undergo other reactions such as dimerizations and polymerizations.

Laccases of any origin, both plant and fungal or animal origin, can be used according to the invention. Their main advantage is that they are simple to use, it being possible in particular for the reaction to be carried out in an open reactor, and they do not require dangerous cooxidants. They can also operate within broad temperature and pH ranges.

The mechanism of the oxidative coupling reaction catalyzed by the enzyme, underlying the entirely advantageous obtaining of a single reaction product, which is characterized by a single type of bond between the base monomer fragments of the polymer, also leaving free the hydroxyl functions of the phenol rings, will not be presumed here. However, it may be assumed that the choice, made by the present inventors, of Y, Y', and where appropriate $Y_1$, deconjugating groups in the para position with respect to the hydroxyl on the phenol ring contributes, with the particular $R_1$, $R'_1$, $R_2$, $R'_2$, $R_3$ and $R'_3$ groups, to stabilizing the radical formed by the oxidase in position 5 of the phenol ring.

The oligomerization step can be carried out using a single monomer of general formula (I), or a plurality of such monomers, for example two or three different macropolyphenols of general formula (I). In this case, the various macropolyphenols can be introduced into the reaction medium in equivalent or different amounts, depending on the phenol polymer targeted.

In particular, the mixture of initial monomers may comprise any combination of macropolyphenol types, for example two or more macrobisphenols, one or more macrobisphenols and one or more macrotrisphenols, etc.

Moreover, when at least one of the starting monomers is not a macrobisphenol, but for example a macrotrisphenol, crosslinking points between various macropolyphenol fragments are created in the polymer chain, thus advantageously forming a three-dimensional crosslinked polymer of phenolic resin type.

In particular embodiments of the invention, the oligomerization step is carried out in an aqueous solution, and under at least one of the following conditions:
  at a temperature of between 0 and 75° C., preferably between 20 and 60° C., and preferentially at approximately 40° C.,
  at a pH of between 3 and 8.

The aqueous solution may also comprise from 0 to 80% by volume of an organic solvent. A wide range of organic solvents may in particular be used, in particular, but not limitingly, alcohols, alkanes, ethers, aromatic solvents, amines, etc.

In other particular embodiments of the invention, the oligomerization step is carried out in an ionic liquid. Such a characteristic proves in particular to be entirely advantageous when one or more of the macropolyphenols of general formula (I), intended to be part of the makeup of the phenol polymer according to the invention, are unstable in an aqueous medium.

Any ionic liquid known to those skilled in the art can be used for this purpose. By way of examples, mention may be made of the following ionic liquids:

[Emim] [EtSO$_4$] (1-ethyl-3-methylimidazolium, ethyl sulfate),
[Emim] [EtSO$_4$] (1-ethyl-3-methylimidazolium, ethyl sulfate),
[TMA] [TfO] (tetramethylammonium trifluoromethanesulfonate),
[C$_6$mim] [AOT]=1-hexyl-3-methylimidazolium, 1,4-bis(2-ethylhexoxy)-1,4-dioxobutane-2-sulfonate (documents)),
[3-butyl-1-[1R,2S,5R)-(−)-menthoxymethyl]imidazolium] [NTf$_2$], (3-butyl-1-[(1R,2S,5R)-(−)-menthoxymethyl]-imidazolium, bis(trifluoromethanesulfonyl)imide),
[1-[(1R,2S,5R)-(−)-menthoxymethyl]-3-methylpyridinium] [NTf$_2$] (1-[(1R,2S,5R)-(−)-menthoxymethyl]-3-methylpyridinium, bis(trifluoro-methanesulfonyl)imide),
[heptyl[(1R,2S,5R)-(−)-menthoxymethyl]dimethylammonium]-3-methylpyridinium] [NTf$_2$] (heptyl[(1R,2S,5R)-(−)-menthoxymethyl]dimethylammonium, bis(trifluoromethanesulfonyl)imide),
[decyl[(1R,2S,5R)-(−)-menthoxymethyl]dimethylammonium] [NTf$_2$] (decyl[(1R,2S,5R)-(−)-menthoxymethyl]dimethylammonium, bis(trifluoromethanesulfonyl)imide).

Preferentially, a minimal amount of laccase of 2 units per millimol of macropolyphenol is used, in order to obtain a degree of conversion of the macropolyphenol of greater than or equal to 70%.

According to another aspect, the invention relates to a composition comprising a polymer according to the invention, in a carrier chosen according to the particular application targeted, for example in a cosmetically acceptable carrier, or else in a polymer matrix or a composite matrix.

The polymer according to the invention may in particular be incorporated into various solutions, in particular food solutions, emulsions or creams, as an antioxidant/free-radical scavenger and/or antimicrobial agent. It may otherwise be incorporated into polymer matrices or composite matrices, for example by reactive extrusion or by means of an internal mixer, so as to confer on said matrices antioxidant/free-radical scavenging and/or plasticizing properties.

The polymer according to the invention may also be covalently or noncovalently deposited on a polymer, composite or metal surface, so as to confer on this surface antioxidant/free-radical scavenging and/or antimicrobial properties. Thus, the present invention also relates to a part of which a surface is coated with a layer made up of a polymer according to the invention. This layer can be both continuous and discontinuous. The polymer according to the invention may in particular be covalently bound to the surface of the part, in particular by chemical grafting.

The polymer according to the invention, in particular obtained from a macrobisphenol, has a high antioxidant potential, which makes it in particular entirely suitable for applications in the cosmetology, food packaging, detoxification, food-processing, etc., fields.

Thus, according to the invention, this polymer can be used as an antioxidant, for inhibiting the oxidation of a substance, by bringing the polymer into contact with this substance.

In particular, it has been demonstrated by the present inventors, by means of the test well known under the name DPPH (for 1,1-diphenyl-2-pycrylhydrazyl) for measuring the antioxidant/free-radical scavenging activity of substances, that the linear polymers in accordance with the invention, of respective formulae (IVa), (IVb), (IVc) and (IVd), have an antioxidant power greater than that of ferulic acid.

The present invention also relates to the use of a polymer in accordance with the invention as a plasticizer.

The polymer according to the invention also has applications as a chelating agent, or else as an antimicrobial agent. In that, it is in particular entirely suitable for surface-treatment applications.

The characteristics and advantages of the invention will emerge more clearly in the light of the exemplary embodiments below, provided by way of simple and in no way limiting illustration of the invention, with the support of FIGS. 1 to 14, wherein.

Figure 13:
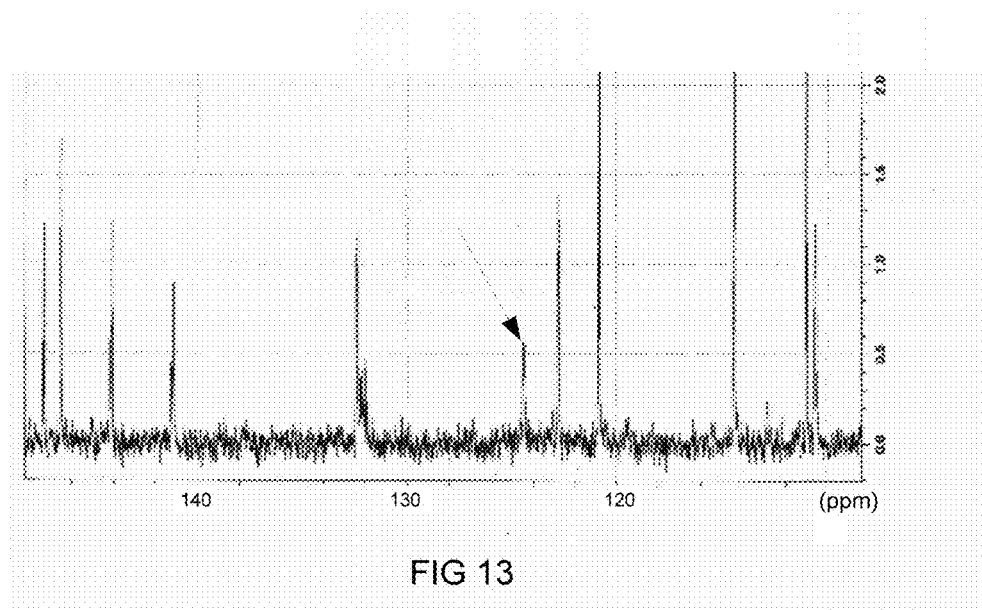
FIG. 13 shows a $^{13}C$ NMR spectrum of a polymer formed by means of a synthesis process in accordance with the invention, from BDF and IDF macropolyphenols.
Figure 14:
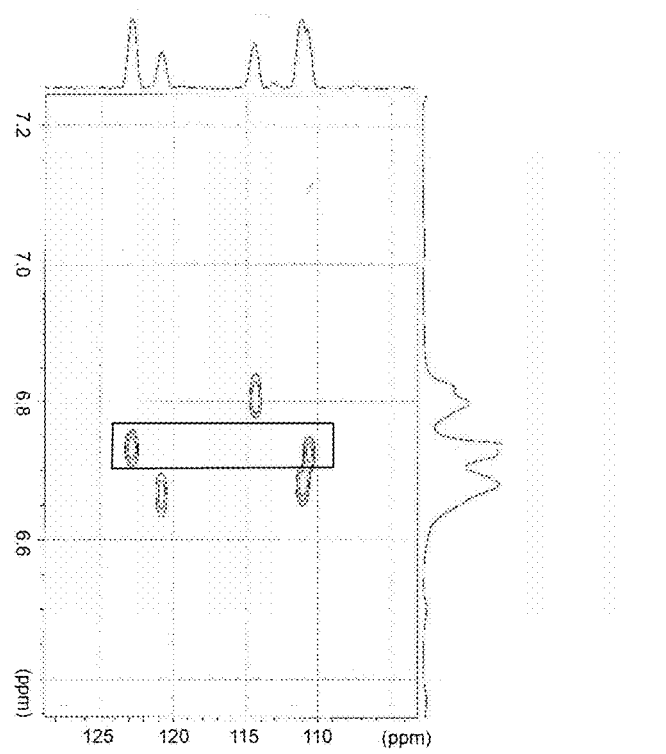

and FIG. 14 shows a 2D NMR spectrum ($^{1}H/^{13}C$ correlation) of the polymer of FIG. 13.

A/SYNTHESIS OF THE PHENOL POLYMERS

A.1/Macrobisphenol Monomers

The following monomers (Ia) (glycerol-3-di(dihydroferulate), termed GDF), (Ib) (butane-1,4-di(dihydroferulate), termed BDF), (Ic) (isosorbide-2,5-(dihydroferulate), termed IDF) and (Id) (propane-1,3-di(dihydroferulate), termed PDF) are used for the synthesis of phenol polymers in accordance with the invention:

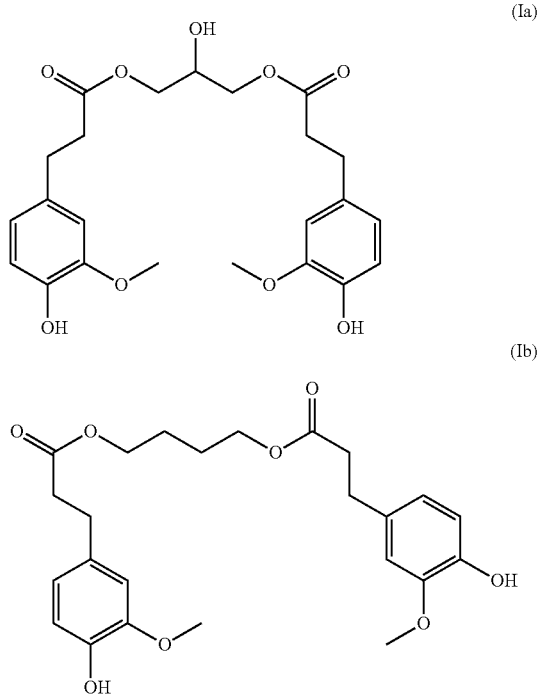

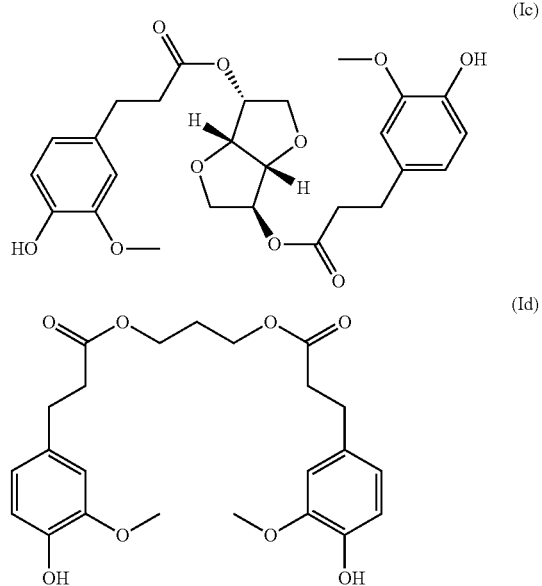

The macrotrisphenol of general formula (Ie) below is also used as a monomer for the synthesis of phenol polymers in accordance with the invention:

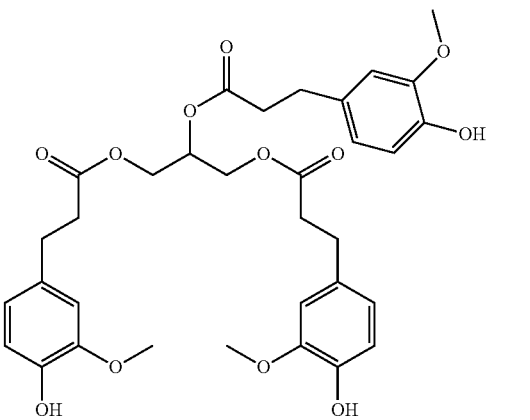

These monomers are prepared according to the process described in the publication by Pion et al., 2013, by means of a lipase B, from ferulic acid and polyols.

A.2/Polymer Synthesis Protocol

The polymers are synthesized by oligomerization of the monomers above, by means of a laccase, which forms a radical on each phenol ring, thus enabling the oligomerization by "radical-radical" coupling.

The general procedure is the following.

The macrobisphenol or the macrotrisphenol is weighed into a round-bottomed flask and then dissolved in the cosolvent chosen, before adding thereto water, optionally buffered to obtain the desired pH, and then the laccase of *Trametes versicolor*, at a chosen load dissolved in water, optionally buffered to obtain the desired pH. The medium is vigorously magnetically stirred for a chosen time, at a chosen temperature and in the open air or under an oxygen atmosphere.

When a solid is present at the end of the reaction, it is recovered and then dried. Otherwise, the reaction medium is taken up in a volume of dichloromethane or of ethyl acetate, equal to 3 times the reaction volume, so as to extract therefrom the organic compounds, i.e. the polymer formed and, where appropriate, the unreacted macrobisphenol or macrotrisphenol. The resulting organic phase is dried in the presence of anhydrous magnesium sulfate ($MgSO_4$), filtered and concentrated under vacuum.

Depending on the starting monomer, the respective polymers (IVa), (IVb), (IVc) and (IVd) described above are thus obtained, as is, starting from the macrotrisphenol of formula (Ie), a branched polymer comprising exclusively 5,5-biaryl bonds between the base macrotrisphenol fragments.

Various experiments were thus carried out with, for each monomer, various combinations of the following reaction conditions:
cosolvent chosen from: methanol, ethanol, isopropanol, tert-butanol, butanol, benzyl alcohol, ethylene glycol, hexane, heptane, dichloromethane, 1,4-dioxane, tetrahydrofuran, acetone, 4-methyl-2-pentanone, ethyl acetate (EtOAc), diethyl ether, 1,2-dimethyl ether, diethyl succinate, dimethylformamide, chloroform, pyridine, benzene, o-dichlorobenzene or acetonitrile;
aqueous solution, for example of Milli-Q® water, which is pure or buffered with a buffer chosen from phosphate buffers and sodium acetate buffers, for a pH of between 2 and 7, more precisely of 2.3, 2.9, 3.7, 3.9, 4.2 or 5.6;
% of cosolvent in the aqueous solution of between 0 and 100% by volume, more particularly of 0, 20%, 25%, 29%, 30%, 40%, 45%, 60%, 80% or 100% (v/v);
macrobisphenol concentration in the solution of between 3 and 50 g/l, more particularly equal to 3.2, 6.4, 6.5, 13, 16.6, 20, 25, 27, 33, 33.33, 43, 45 or 50 g/l;
laccase load of between 2 and 1000 units per millimol of macrobisphenol, more particularly equal to 2, 10, 50, 100, 200 or 1000 u/mmol;
temperature of between 0 and 80° C., more particularly equal to 5, 20, 40, 50, 60 or 80° C.;
time of between 8 and 120 h, more particularly equal to 8, 18, 24, 48, 72, 96 or 120 h.

By way of particular examples, the following polymers are formed under the conditions indicated in table 1 below:

a PLgel 5 µm 100, 600×7.5 mm column and a PDA 3000 UV detector from Dionex.

The vector used is tetrahydrofuran at a flow rate of 1 ml/min, and the detection is carried out at 250 nm.

The calibration of the analytical device is carried out by means of Igepal® standards.

Figure 1A:
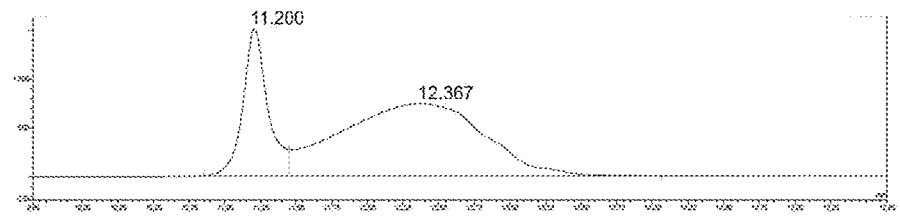
FIG. 1a shows a chromatograph obtained by size exclusion chromatography for a polymer B1 formed by a synthesis process in accordance with the invention, with detection at 250 nm.
Figure 1B:
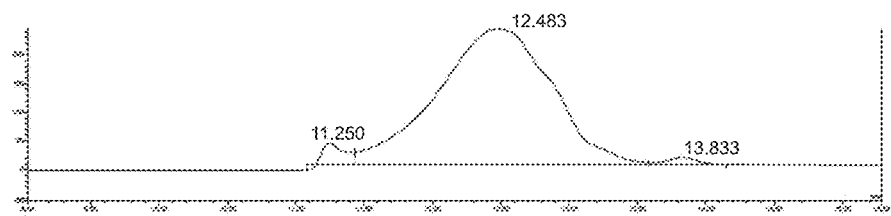
FIG. 1b shows a chromatograph obtained by size exclusion chromatography for a polymer P1 formed by a synthesis process in accordance with the invention, with detection at 250 nm.
Figure 1C:
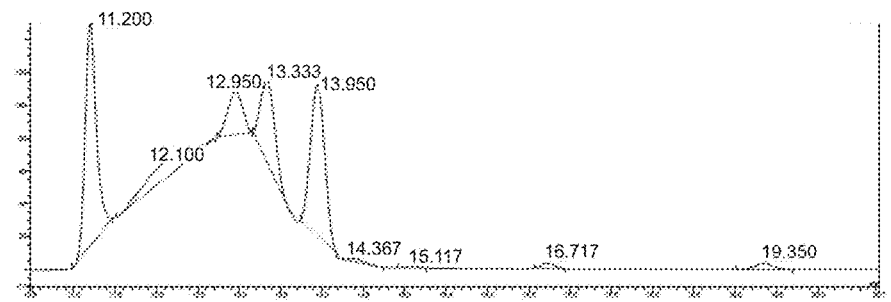
FIG. 1c shows a chromatograph obtained by size exclusion chromatography for a polymer G1 formed by a synthesis process in accordance with the invention, with detection at 250 nm.

By way of example, the spectra obtained for the polymers in accordance with the present invention B1, formed from the BDF monomer, P1, formed from the PDF monomer, and G1, formed from the GDF monomer, as indicated above, are shown respectively in FIGS. 1a, 1b and 1c. A virtually total conversion of the monomer, a good dispersity of the HPSEC signal, and a relatively high degree of polymerization are observed therein, for each polymer in accordance with the invention. Each of the polymers according to the invention is largely predominant in the corresponding mixture obtained.

Figure 2A:
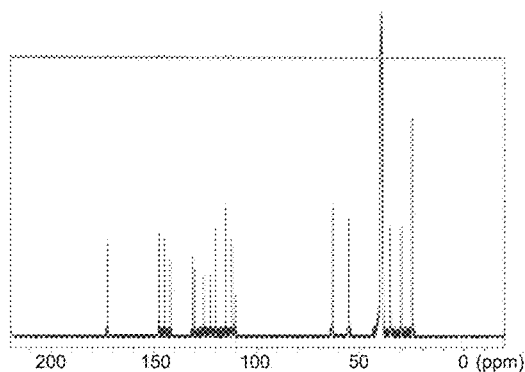
FIG. 2a shows a $^{13}$C NMR spectrum of a polymer B1 formed by a synthesis process in accordance with the invention.
Figure 2B:
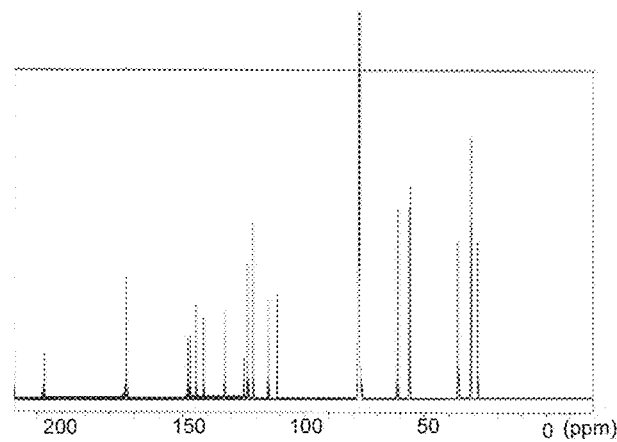
FIG. 2b shows a $^{13}$C NMR spectrum of a polymer P1 formed by a synthesis process in accordance with the invention.
Figure 2C:
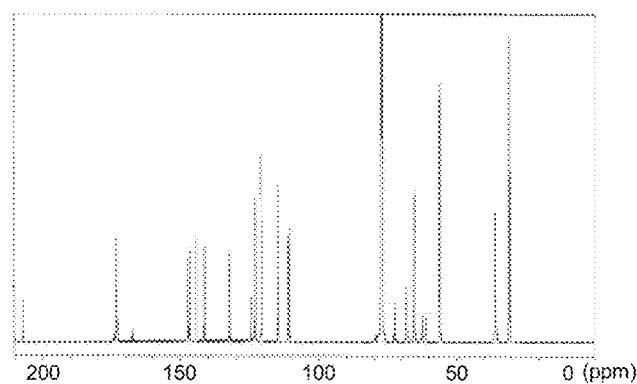
FIG. 2c shows a $^{13}$C NMR spectrum of a polymer G1 formed by a synthesis process in accordance with the invention.

The $^{13}C$ NMR spectra of each of these polymers in accordance with the invention were also produced (DMSO-$d_6$ or $CDCl_3$), and are shown respectively in FIGS. 2a, 2b and 2c for the polymers B1, P1 and G1.

Figure 2D:
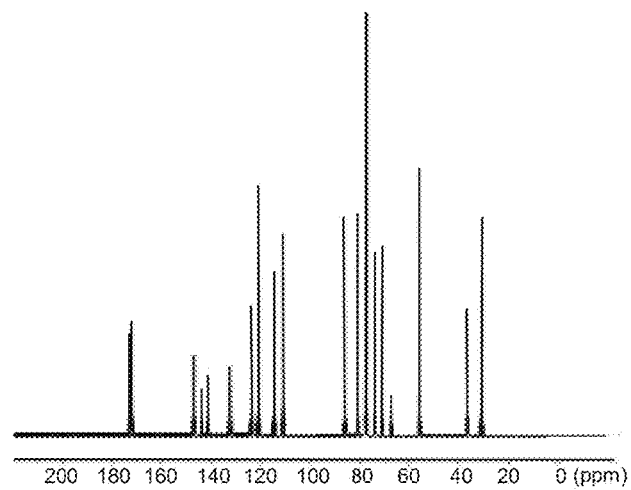
FIG. 2d shows a $^{13}$C NMR spectrum of a polymer I1 formed by a synthesis process in accordance with the invention.

A $^{13}C$ NMR spectrum was also produced for a polymer, called I1, obtained in accordance with the invention with the IDF macrobisphenol as monomer. This spectrum is shown in FIG. 2d.

Figure 2E:
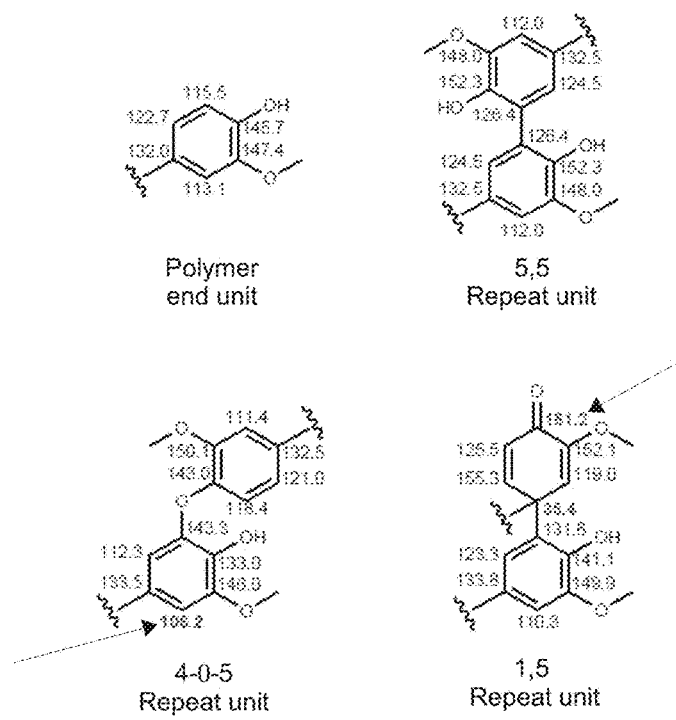
FIG. 2e shows the $^{13}$C NMR chemical shifts, in ppm, predicted by simulation using the ChemBiodrawUltra 13.0.2® software, for various types of bond between phenol units.

All of these spectra were compared to the chemical shifts predicted by simulation using the ChemBiodrawUltra 13.0.2® software, for various types of bond between the phenol units, which are shown in FIG. 2e. This comparison clearly demonstrates that the bonds in the polymers B1, P1 and G1 are indeed of the 5,5-biaryl type. Indeed, there is, on the spectra of these polymers, no peak characteristic of a 1,5 bond, at 181.2 ppm, and no peak characteristic of a 4-O-5 bond, at 106.2 ppm.

Figure 3:
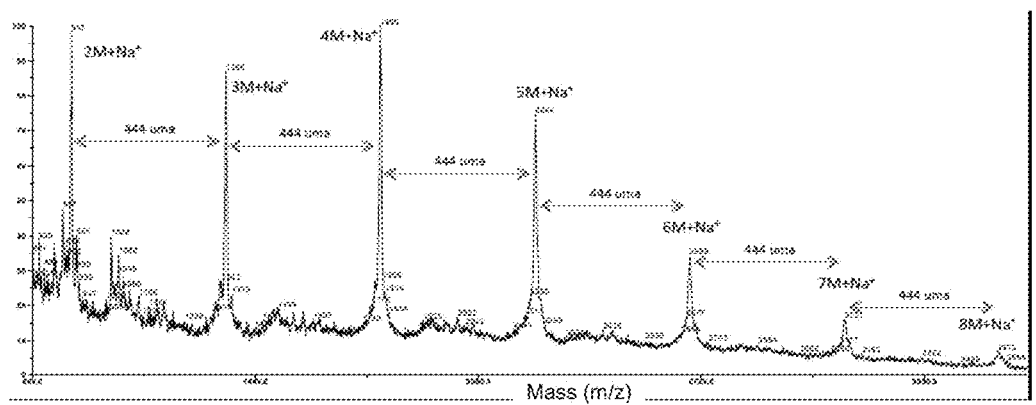
FIG. 3 shows the results obtained by MALDI-TOF analysis of a polymer B1 formed by a synthesis process in accordance with the invention.

MALDI-TOF analyses were also carried out on the polymers in accordance with the invention B1, P1 and G1. The result obtained for the polymer B1 is shown in FIG. 3. A regular sequence and a maximum degree of polymerization equal to 8 are observed therein for this polymer. This result is representative of that obtained for the polymers P and G1, and also for all the polymers obtained by means of a synthesis process in accordance with the invention.

TABLE 1

Reaction conditions for obtaining polymers in accordance with the invention

| Polymer | Monomer | Solvent (% v/v) | pH | Monomer concentration (g/l) | Laccase (u/mmol) | Temp. (° C.) | Time (h) |
|---|---|---|---|---|---|---|---|
| P1 | PDF | EtOH (30) | — | 20 | 100 | 40 | 120 |
| B1 | BDF | Acetone (45) | 4.2 | 6.5 | 1000 | 20 | 120 |
| G1 | GDF | Acetone (25) | 4.2 | 25 | 10 | 40 | 96 |
| PDF 1000 | PDF | EtOAc (40) | 3.7 | 33.33 | 50 | 20 | 72 |
| PDF 1500 | PDF | EtOAc (20) | 3.7 | 33.33 | 50 | 20 | 72 |

A.3/Analysis of the Products Obtained According to the Operating Parameters

For each experiment, a size exclusion chromatography (HPSEC) analysis is carried out in order to determine the degree of conversion, and the molecular weight distribution curve and to evaluate the average molecular weights of the products obtained, by means of a device comprising a Gilson 305 pump, an UltiMate® 3000 ACC injector from Dionex, All of the spectra obtained show that, for all the operating parameter combinations, a linear and homogeneous polymer, characterized by a single type of 5,5-biaryl bond between the macrobisphenol monomers, is very predominantly obtained.

On the basis of the spectra obtained, the influence of the various operating parameters on the polymer formed was studied.

Influence of the Solvent

The degree of conversion of the base monomer to polymer in accordance with the invention was evaluated for the PDF monomer, by varying respectively in the % of cosolvent, the pH of the reaction medium and the nature of the cosolvent.

Figure 4:
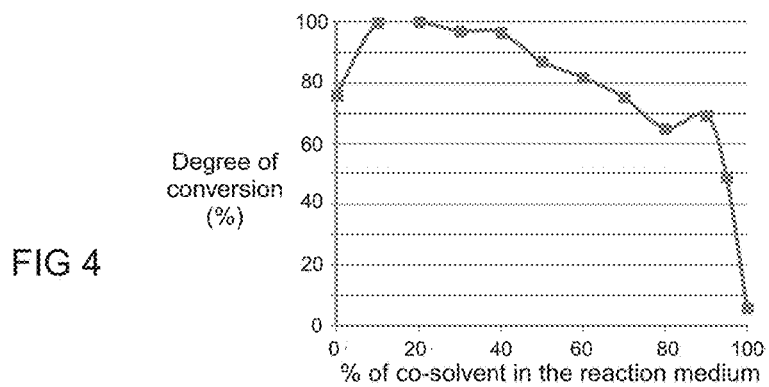
FIG. 4 shows the evolution of the degree of conversion of the PDF monomer to linear polymer by means of a synthesis process in accordance with the invention, as a function of the % of ethyl acetate cosolvent in the aqueous reaction solution.
Figure 5:
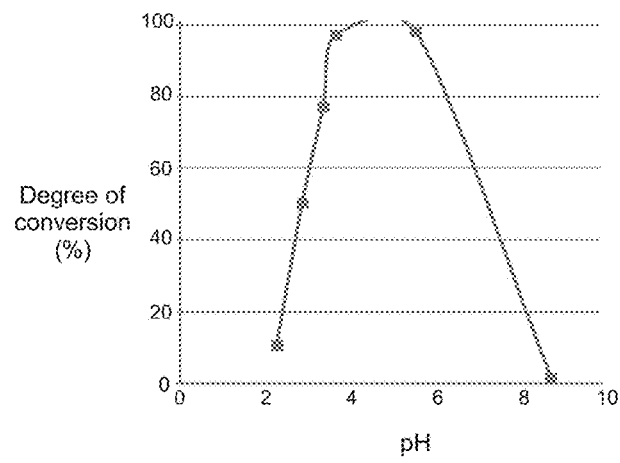
FIG. 5 shows the evolution of the degree of conversion of the PDF monomer to linear polymer by means of a synthesis process in accordance with the invention, as a function of the pH of the aqueous reaction solution, with ethyl acetate as cosolvent.
Figure 6:
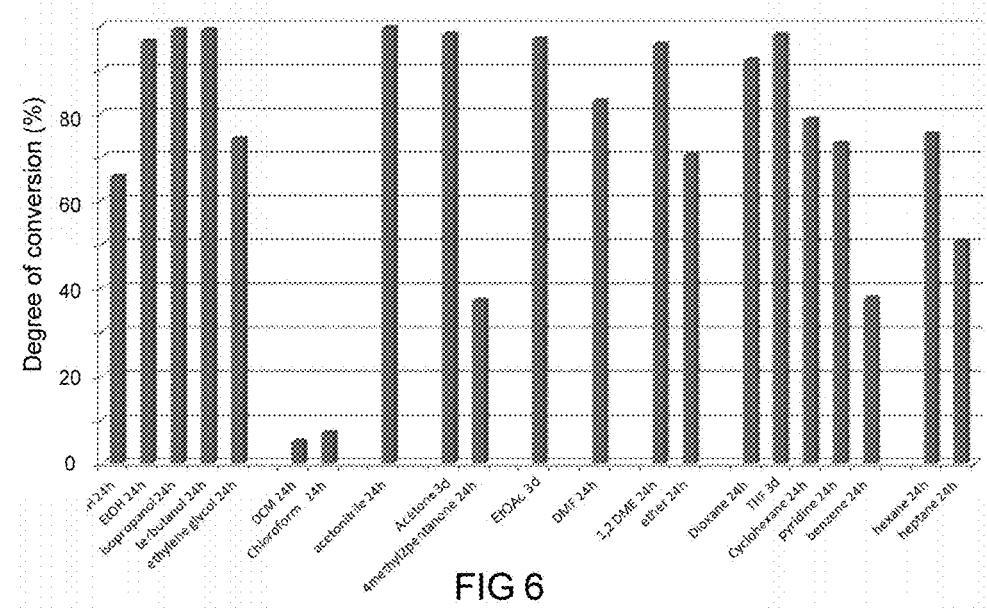
FIG. 6 shows the evolution of the degree of conversion of the PDF monomer to linear polymer by means of a synthesis process in accordance with the invention, as a function of the nature of the cosolvent in the aqueous reaction solution, the % of cosolvent in the latter being 30% (v/v)

The results are shown respectively in FIG. 4 (variation in the % of solvent, the operating conditions being the following: cosolvent EtOAc, temperature 20° C., pH 3.7, monomer concentration 1 g/30 ml), FIG. 5 (variation in the pH, the operating conditions being the following: cosolvent EtOAc at 30% v/v, temperature 20° C.) and FIG. 6 (variation in the nature of the cosolvent, the operating conditions being the following: 30% v/v of cosolvent, temperature 20° C., pH 3.7, time indicated on the graph after the name of the cosolvent). These results are representative of those obtained for all the other starting monomers, and all the operating conditions combinations. They demonstrate that the process of oligomerization catalyzed by the laccase can advantageously be carried out with a wide range of cosolvents, in a wide pH range, and both in a strict aqueous medium and in a mixed water/cosolvent medium, this being up to high proportions of cosolvent.

Influence of the Reaction Time

The influence of the reaction time was evaluated using the BDF monomer, under the following operating conditions: temperature of 20° C., laccase load of 50 u/mmol, pH of 4.2, acetone cosolvent at 60% (v/v), initial concentration of monomer of 6.4 g/l. Reaction times between 8 and 120 h were tested.

Figure 7:
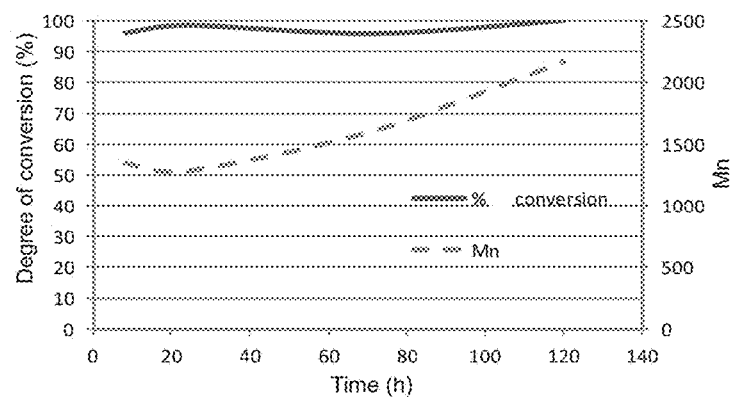
FIG. 7 shows a graph representing, as a function of the reaction time, the degree of conversion of the BDF monomer and the number-average molecular weight (Mn) of the linear polymer obtained by means of a synthesis process in accordance with the invention.

The results obtained, in terms of degree of conversion of the monomer and of number-average molecular weight, as a function of the reaction time, are shown in FIG. 7. It is observed therein that the maximum degree of conversion is very rapidly reached during the reaction, whereas the number-average molecular weight increases continuously with the reaction time. This demonstrates that the dimerization of the BDF monomer is rapid, the oligomerization taking a little longer to be carried out. Controlling the reaction time thus makes it possible to control the degree of polymerization.

These results are representative of those obtained for all the other starting monomers, and all the operating conditions combinations.

Influence of the Dilution

The influence of the dilution of the monomer in the reaction medium was analyzed for the BDF monomer, under the following operating conditions: temperature of 20° C., laccase load of 50 u/mmol, pH of 4.2, acetone cosolvent at 60% (v/v), reaction time of 5 days. Initial concentrations of monomer of 3.2, 6.4 and 12.8 g/l were tested.

Figure 8:
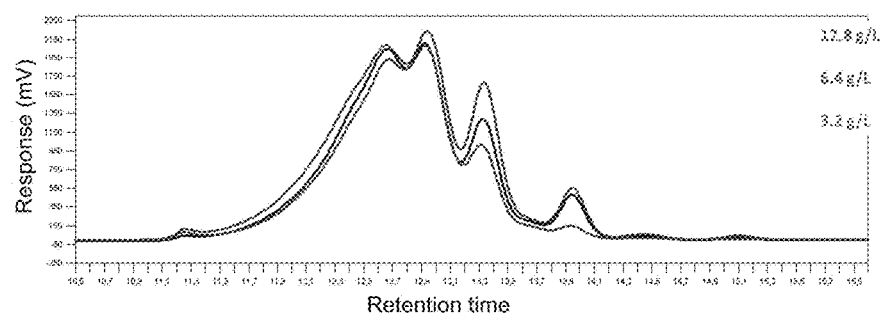
FIG. 8 shows the spectra obtained by size exclusion chromatography for linear polymers formed from the BDF monomer by means of the synthesis processes in accordance with the invention, using various concentrations of monomer in the reaction medium.

For each of the reactions, the spectra obtained by size exclusion chromatography are shown in FIG. 8. It is observed therein that the dilution has a negligible influence on the reaction product obtained. These results are representative of those obtained for all the other starting monomers, and all the operating condition combinations.

Influence of the Temperature

The influence of the temperature was analyzed using the GDF and IDF monomers, respectively, under the following operating conditions: monomer concentration of 28 g/l, laccase load of 50 u/mmol, pH of 4.2, acetone or ethanol (EtOH) cosolvent at 30% (v/v), reaction time of 5 days. Temperatures of between 20 and 80° C. were tested.

Figure 9:
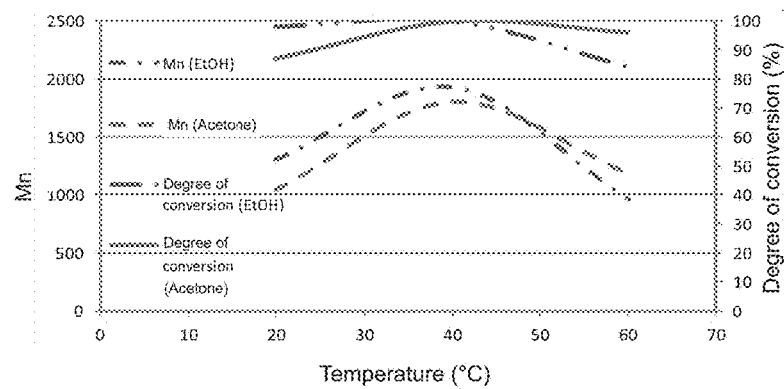
FIG. 9 shows a graph representing, as a function of the temperature applied, the degrees of conversion of the GDF monomer and the number-average molecular weights (Mn) of the linear polymers obtained by means of synthesis processes in accordance with the invention using, as cosolvent, respectively acetone and ethanol (EtOH)
Figure 10:
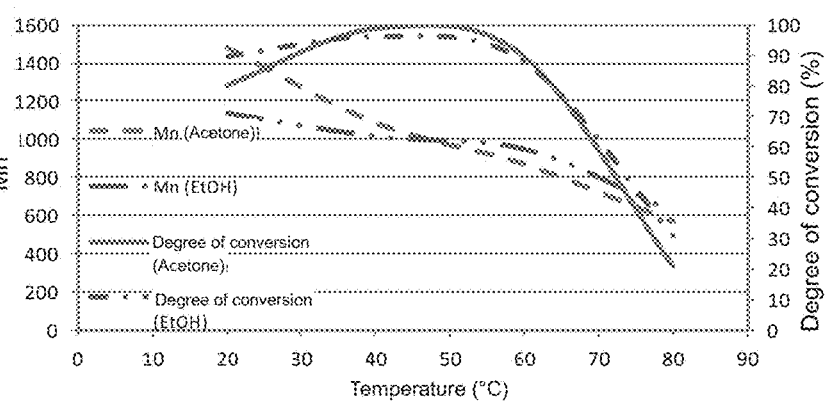
FIG. 10 shows a graph representing, as a function of the temperature applied, the degrees of conversion of the IDF monomer and the number-average molecular weights (Mn) of the linear polymers obtained by means of synthesis processes in accordance with the invention using, as cosolvent, respectively acetone and ethanol (EtOH)

The results obtained, in terms of degree of conversion of the monomer and of number-average molecular weight (Mn), as a function of the temperature and for each monomer and each solvent, are shown in FIG. 9 for the GDF monomer and in FIG. 10 for the IDF monomer. It is observed therein that the polymerization reaction occurs for temperatures up to approximately 75° C., with an optimal temperature range of between 20 and 60° C., and an optimal value of approximately 40° C.

These results are representative of those obtained for all the other starting monomers, and all the operating conditions combinations.

Influence of the Laccase Load

The influence of the temperature was analyzed using the GDF and IDF monomers, respectively, under the following operating conditions: monomer concentration of 28 g/l, pH of 4.2, acetone cosolvent at 30% (v/v), reaction time of 5 days, temperature of 20° C. Laccase loads of between 0 and 1100 u/mmol were tested.

Figure 11:
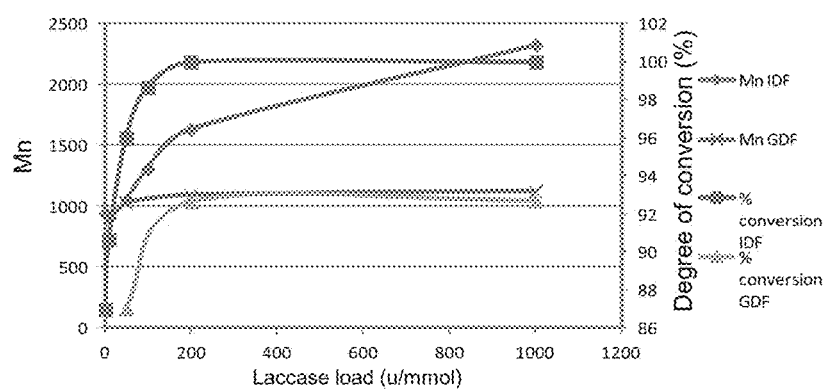
FIG. 11 shows a graph representing, as a function of the laccase load used, for each of the respective GDF and IDF monomers, the degree of conversion and the number-average molecular weight (Mn) of the linear polymer obtained by means of a synthesis process in accordance with the invention.

The results obtained, in terms of degree of conversion of the monomer and of number-average molecular weight (Mn), as a function of the laccase load and for each monomer, are shown in FIG. 11. It is observed therein that the population of the peaks at high molecular weight increases rapidly with the enzyme load, at least for IDF. The minimum amount of laccase required for a degree of conversion greater than or equal to 70% is 2 u/mmol of macrobisphenol monomer.

These results are representative of those obtained for all the other starting monomers, and all the operating conditions combinations.

A.4/Synthesis of a Copolymer in Accordance with the Invention from Macrobisphenols A copolymer in accordance with the invention was prepared from the BDF and IDF macrobisphenols and according to the following procedure.

The BDF (0.5 g) and IDF (0.5 g) macrobisphenols are weighed into a round-bottomed flask and then dissolved in 20 ml of acetonitrile, before adding thereto milli-Q® water and then the laccase of *Trametes versicolor* (15.6 mg; 100 u/mmol$_{substrate}$) dissolved in water, the cosolvent/milli-Q® water final volume ratio being 3/7. The medium is vigorously magnetically stirred for 24 hours, at ambient temperature and in the open air. After 24 hours, a yellow oil formed at the bottom of the round-bottomed flask.

The reaction medium is taken up in a volume of dichloromethane or of ethyl acetate equal to 3 times the reaction volume, so as to extract therefrom the organic compounds (oligomers formed and unreacted starting reagents). The resulting organic phase is dried in the presence of anhydrous magnesium sulfate ($MgSO_4$), filtered and concentrated under vacuum. A beige solid is obtained.

The $^{13}C$ NMR spectrum of the resulting copolymer was produced (DMSO-$d_6$ or $CDCl_3$), and is shown in FIG. 13. A peak at 124.47 ppm, indicated by an arrow in the figure, characteristic of 5,5-biaryl bonds, is observed therein.

An analysis by two-dimensional NMR spectrometry ($^1H$/$^{13}C$ correlation) was also carried out. The spectrum obtained is shown in FIG. 14. It is characteristic of phenol polymers of which the biaryl bonds are solely of the 5,5 type. The two signals representative of the two phenol CH of the aromatic rings forming the 5,5-biaryl bonds (corresponding to the 5,5 repeat unit shown in FIG. 2e) are in particular observed, in the box.

These analysis results confirm the formation of a copolymer with exclusively 5,5-biaryl bonds.

A.5/Synthesis of a Copolymer in Accordance with the Invention from a Macrobisphenol and from a Macrotrisphenol A copolymer in accordance with the invention was prepared from the PDF macrobisphenol and from the GTF macrotrisphenol according to the following procedure.

The PDF macrobisphenol (0.5 g) and the GTF macrotrisphenol (0.5 g) are weighed into a round-bottomed flask and then dissolved in 10 ml of acetonitrile, before adding thereto milli-Q® water, and then the laccase of *Trametes versicolor* (15.6 mg; 100 u/mmol$_{substrate}$) dissolved in water, the cosolvent/milli-Q® water final volume ratio being 3/7. The medium is vigorously magnetically stirred for 24 hours, at ambient temperature and in the open air. After 24 hours, the reaction medium turned dark brown.

The reaction medium is taken up in a volume of dichloromethane or of ethyl acetate equal to 3 times the reaction volume, so as to extract therefrom the organic compounds (oligomers formed and unreacted starting reagents). The resulting organic phase is dried in the presence of anhydrous magnesium sulfate (MgSO$_4$), filtered and concentrated under vacuum. A brown solid is obtained.

B/ANALYSIS OF THE ANTIOXIDANT POWER OF THE PHENOL POLYMERS

The antioxidant power of the phenol polymers in accordance with the invention PDF 1000 and PDF 1500 was evaluated using the DPPH test, according to the protocol described in the publication by Brand-Williams et al., 1995 (*Food Sci. Technol-Leb*, 28, 25).

By way of comparative examples, the antioxidant power of ferulic acid, and that of the compounds well known for their antioxidant power: butylhydroxyanisole (BHA), butylhydroxytoluene (BHT), gallic acid and gentisic acid, were tested under equivalent conditions.

For each substance to be analyzed, concentrations between 0.12 and 0.00125×10$^{-3}$ mol/l, in ethanol (77 µl) as solvent, were tested in the presence of 3 ml of a solution in ethanol of DPPH (i.e. a DPPH concentration of 6×10$^{-5}$ mol/l). For each sample, the absorbance was measured as a function of time, and the % of DPPH remaining in solution was calculated.

The results obtained after 435 min of reaction, i.e. until a stable value corresponding to a plateau is reached, are shown in table 2 below.

TABLE 2

Values obtained in a DPPH test for phenol polymers in accordance with the invention

| Polymer | Concentration (×10$^{-3}$ mol/l) | Optical absorbance of the DPPH | % of DPPH remaining |
|---|---|---|---|
| PDF 1000 | 0.03 | 0.5 | 13.88 |
| | 0.01 | 0.16 | 22.71 |
| | 0.005 | 0.083 | 46.53 |
| | 0.0025 | 0.042 | 70.19 |
| | 0.00125 | 0.021 | 85.33 |
| PDF 1500 | 0.03 | 0.5 | 13.56 |
| | 0.01 | 0.16 | 16.88 |
| | 0.005 | 0.083 | 33.28 |
| | 0.0025 | 0.042 | 59.46 |
| | 0.00125 | 0.021 | 80.44 |

The concentration of each compound making it possible to reduce by 50% the initial amount of DPPH (EC50) is deduced from the data obtained. This concentration is indicated in table 3 below.

TABLE 3

EC50 concentrations measured using a DPPH test

| Compound | PDF 1000 | PDF 1500 | Ferulic acid | BHA | BHT | Gallic acid | Gentisic acid |
|---|---|---|---|---|---|---|---|
| EC50 | 0.0865 | 0.069 | 0.38 | 0.24 | 0.24 | 0.08 | 0.09 |

These results clearly show that the phenol polymer compounds in accordance with the invention PDF 1000 and PDF 1500 have an antioxidant power greater not only than ferulic acid, but also than the commonly used antioxidants BHA, BHT, gallic acid and gentisic acid.

C/PHENOL POLYMER TOXICITY TEST

A test for toxicity with respect to estrogen receptors was carried out for the IDF, PDF, GDF and BDF macrobisphenols, according to the method set out in the publication by Molina-Molina et al., 2008 (*Toxicol. Appl. Pharmacol.*, doi: 10.1016/j.taap.2008.07.017), on the HELN-ERα cell line, described in the publication by Escande et al., 2006 (*Biochemical Pharmacology*, 71, 1459-1469).

Figure 12:
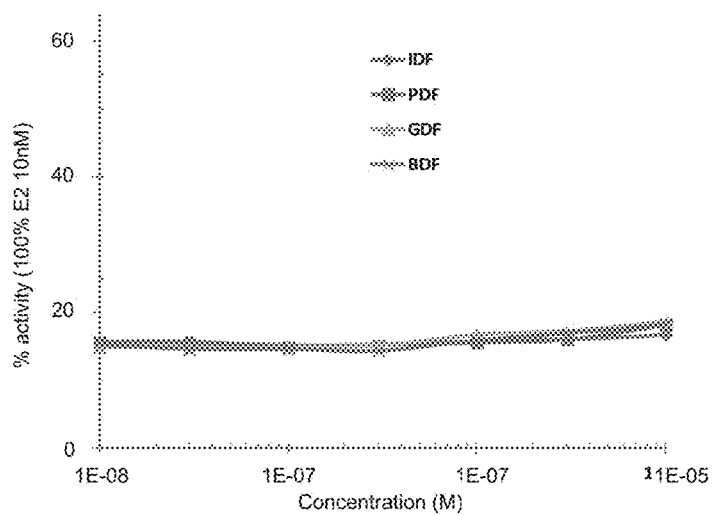
FIG. 12 shows a graph representing, for macrobisphenols corresponding to formula (I), called respectively IDF, GDF, BDF and PDF, the % antagonist activity with respect to the activity of estradiol (E2) at 10 nM, as a function of the concentration of the macrobisphenol.

The results obtained, expressed as % of antagonist activity with respect to the activity of estradiol (E2) at 10 nM, as a function of the monomer concentration, are shown in FIG. 12. It is observed therein that the IDF, PDF, GDF and BDF macrobisphenols interact only very little with estrogen receptors. In comparison, the same experiment carried out for commercially available bisphenol A shows that the latter exhibits a percentage activity, at 10$^{-6}$ M, of 45%, and, at 10$^{-5}$ M, of 60%. The IDF, PDF, GDF and BDF macrobisphenols consequently exhibit an action that is much lower than bisphenol A, with respect to estrogen receptors.

It can reasonably be deduced therefrom that the same is true for the polymers in accordance with the invention, of which these macrobisphenols constitute the base monomers.

The invention claimed is:
1. A phenol polymer obtained by oligomerization catalyzed by an enzyme of oxidase type, said phenol polymer comprising a plurality of monomers, said monomers being of one or more macropolyphenol(s), each macropolyphenol having a structure with at least two phenol rings corresponding to general formula (I):

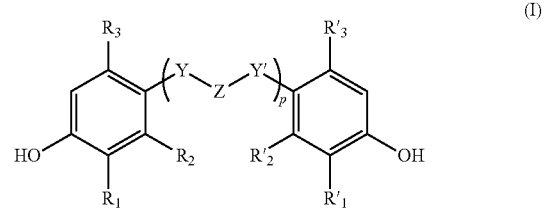

wherein:
p represents an integer between 1 and 30,
R$_1$, R'$_1$, R$_2$, R'$_2$, R$_3$ and R'$_3$, which may be identical or different, each represent a hydrogen atom, a chlorine atom, a bromine atom, an iodine atom, a fluorine atom, or an alkyl, benzyl, Xalkyl, where appropriate substituted, Xbenzyl, where appropriate substituted, Xacyl, B(OR')$_2$, NHR', NO$_2$, SR'O or SO$_2$R' group,
where X represents N, O, S or P
and R' represents an alkyl group or an aryl group,
R$_1$ and R'$_1$ do not represent a hydrogen atom,
Y and Y', which may be identical or different, each represent:
either an oxygen atom, a sulfur atom or a deconjugating group, said deconjugating group comprising neither an epoxide ring, nor an aziridine ring, nor a phenol group which is not substituted on all its carbon atoms, said deconjugating group not comprising a bond conjugated with the phenol ring to which said deconjugating group is bonded, or a group corresponding to formula (II):

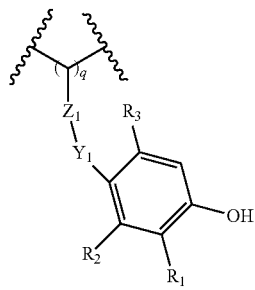

(II)

wherein:
q represents an integer between 1 and 8,
$Y_1$ represents an oxygen atom, a sulfur atom or a deconjugating group, said deconjugating group comprising neither an epoxide ring, nor an aziridine ring, nor a phenol group which is not substituted on all its carbon atoms, said deconjugating group not comprising a bond conjugated with the phenol ring of the group of formula (II),
$Z_1$ represents a heteroatom or a spacer group comprising neither an epoxide ring, nor an aziridine ring, nor a phenol group which is not substituted on all its carbon atoms, nor an alkenyl group, nor an alkynyl group,
and Z represents:
either a heteroatom or a spacer group comprising neither an epoxide ring, nor an aziridine ring, nor a phenol group which is not substituted on all its carbon atoms, nor an alkenyl group, nor an alkynyl group,
or a group corresponding to formula (III):

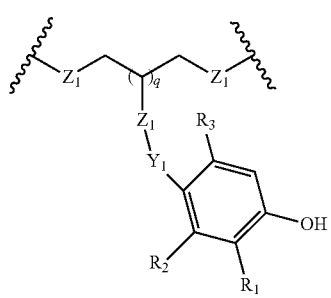

(III)

wherein q represents an integer between 1 and 8,
the bonds between the monomers of the one or more macropolyphenol(s) of general formula (I), within said polymer, being exclusively 5,5-biaryl bonds.

2. The polymer as claimed in claim 1, wherein $R_1$ and/or $R'_1$ represent(s) a linear or branched, saturated hydrocarbon-based radical comprising from 1 to 5 carbon atoms, or an $OR_4$ group, where $R_4$ represents a linear or branched, saturated hydrocarbon-based radical comprising from 1 to 5 carbon atoms.

3. The polymer as claimed in claim 1, wherein $R_2$, $R_3$, $R'_2$ and/or $R'_3$ represent(s) a hydrogen atom.

4. The polymer as claimed in claim 1, wherein Y and/or Y' represent(s) a group of general formula (V):

—$(CH_2)_m$—X'— (V)

wherein:
m is between 1 and 5, and X' represents an oxygen atom or a sulfur atom or a group selected from the group consisting of:

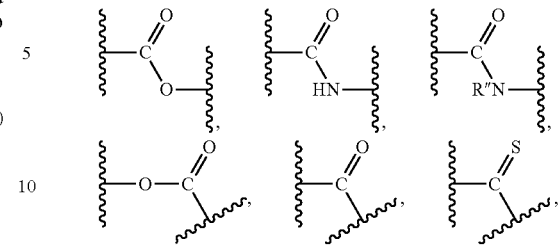

$NR''$, NH and $SO_2$, where R'' represents an alkyl group or an aryl group.

5. The polymer as claimed in claim 1, wherein Y and Y', and where appropriate $Y_1$, each represent a group of general formula (VI):

(VI)

6. The polymer as claimed in claim 1, wherein Z represents a linear or branched, saturated hydrocarbon group, where appropriate substituted, comprising from 1 to 6 carbon atoms, which can comprise one or more heteroatoms, or a saturated cyclic hydrocarbon group, where appropriate substituted, comprising from 1 to 6 carbon atoms, which can comprise a single ring or several condensed rings, and which can comprise one or more heteroatoms.

7. The polymer as claimed in claim 1, corresponding to general formula (IV):

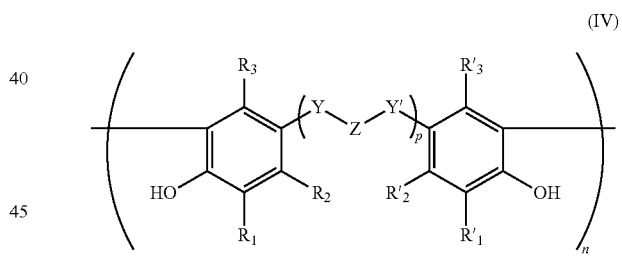

(IV)

wherein n represents an integer between 2 and 100.

8. The polymer as claimed in claim 1, corresponding to one of formulae (IVa), (IVb), (IVc) and (IVd)

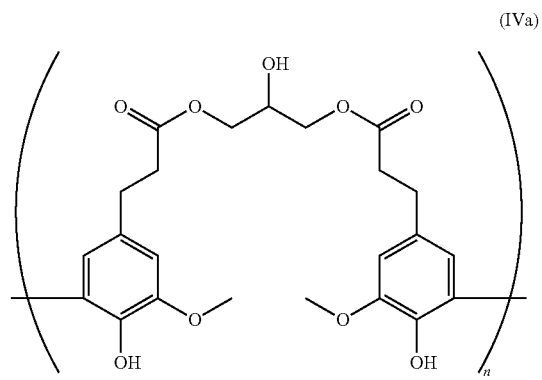

(IVa)

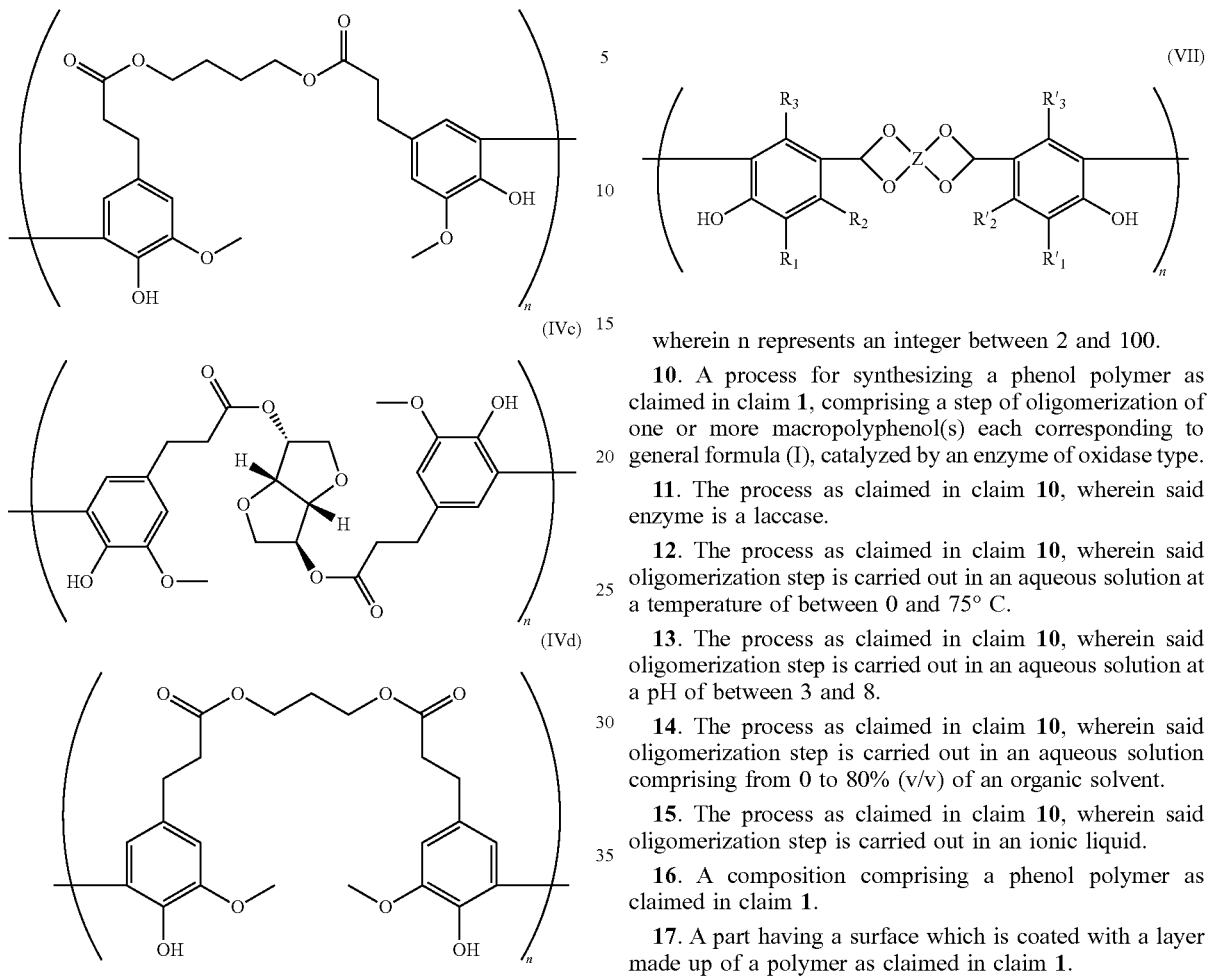

wherein n represents an integer between 2 and 100.

9. The polymer as claimed in claim 1, corresponding to general formula (VII):

wherein n represents an integer between 2 and 100.

10. A process for synthesizing a phenol polymer as claimed in claim 1, comprising a step of oligomerization of one or more macropolyphenol(s) each corresponding to general formula (I), catalyzed by an enzyme of oxidase type.

11. The process as claimed in claim 10, wherein said enzyme is a laccase.

12. The process as claimed in claim 10, wherein said oligomerization step is carried out in an aqueous solution at a temperature of between 0 and 75° C.

13. The process as claimed in claim 10, wherein said oligomerization step is carried out in an aqueous solution at a pH of between 3 and 8.

14. The process as claimed in claim 10, wherein said oligomerization step is carried out in an aqueous solution comprising from 0 to 80% (v/v) of an organic solvent.

15. The process as claimed in claim 10, wherein said oligomerization step is carried out in an ionic liquid.

16. A composition comprising a phenol polymer as claimed in claim 1.

17. A part having a surface which is coated with a layer made up of a polymer as claimed in claim 1.

* * * * *